(12) United States Patent
Chavatte et al.

(10) Patent No.: US 9,114,019 B2
(45) Date of Patent: *Aug. 25, 2015

(54) POROUS CONTAINMENT DEVICE AND ASSOCIATED METHOD FOR STABILIZATION OF VERTEBRAL COMPRESSION FRACTURES

(71) Applicant: DePuy Synthes Products, LLC, Raynham, MA (US)

(72) Inventors: Kris Chavatte, Oberdorf (CH); Markus Weber, Oberdorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 67 days.

This patent is subject to a terminal disclaimer.

(21) Appl. No.: 13/953,186

(22) Filed: Jul. 29, 2013

(65) Prior Publication Data

US 2013/0317613 A1 Nov. 28, 2013

Related U.S. Application Data

(63) Continuation of application No. 12/743,293, filed as application No. PCT/US2008/083350 on Nov. 13, 2008, now Pat. No. 8,518,115.

(60) Provisional application No. 60/988,696, filed on Nov. 16, 2007.

(51) Int. Cl.
*A61F 2/44* (2006.01)
*A61B 17/70* (2006.01)
(Continued)

(52) U.S. Cl.
CPC .............. *A61F 2/44* (2013.01); *A61B 17/7098* (2013.01); *A61B 17/3472* (2013.01); *A61B 2019/307* (2013.01); *A61B 2019/5483* (2013.01)

(58) Field of Classification Search
CPC ........... A61B 17/7098; A61B 17/3472; A61B 2019/5483; A61B 2019/307; A61F 2/44
USPC ...................... 623/17.11–17.16; 606/190, 191
See application file for complete search history.

(56) References Cited

U.S. PATENT DOCUMENTS

| 2,381,050 A | 12/1943 | Hardinge |
| 3,701,703 A | 10/1972 | Zimmer et al. |

(Continued)

FOREIGN PATENT DOCUMENTS

| AU | 702330 B2 | 2/1999 |
| AU | 7711198 A | 3/1999 |

(Continued)

OTHER PUBLICATIONS

Maciunas, R. J., MD, "Endovascular Neurological Intervention", American Association of Neurological Surgeons, 1995, pp. 153-158.

(Continued)

*Primary Examiner* — Pedro Philogene
(74) *Attorney, Agent, or Firm* — Nutter McClennen & Fish LLP

(57) ABSTRACT

A porous containment device for implanting into the interior volume of a targeted vertebral body for use in restoring the anatomy of the targeted vertebral body. The porous containment device is expandable from an insertion configuration to an expanded configuration via, for example, a bone filler material. The porous containment device includes an enlarged proximal portion, an enlarged distal portion, and a narrower central portion located between the enlarged proximal and distal portions. The porous containment device includes at least one pore positioned between a midline of the narrower central portion and walls of the enlarged distal and proximal portions. The porous containment device may include one or more air or fluid evacuation pores to permit air or fluid to escape and internal or external constraints to form the narrower central portion. In addition, a cannulated sleeve may be used to insert the porous containment device.

19 Claims, 6 Drawing Sheets

(51) Int. Cl.
  *A61B 17/34* (2006.01)
  *A61B 19/00* (2006.01)

(56) References Cited

U.S. PATENT DOCUMENTS

| | | | |
|---|---|---|---|
| 3,867,728 A | 2/1975 | Stubstad et al. | |
| 4,055,029 A | 10/1977 | Kalbow et al. | |
| 4,311,146 A | 1/1982 | Wonder | |
| 4,327,736 A | 5/1982 | Inoue | |
| 4,364,392 A | 12/1982 | Strother et al. | |
| 4,735,625 A | 4/1988 | Davidson | |
| 4,755,184 A | 7/1988 | Silverberg | |
| 4,819,637 A | 4/1989 | Dormandy, Jr. et al. | |
| 4,820,349 A | 4/1989 | Saab | |
| 4,969,888 A | 11/1990 | Scholten et al. | |
| 4,986,830 A | 1/1991 | Owens et al. | |
| 5,041,114 A | 8/1991 | Chapman et al. | |
| 5,049,132 A | 9/1991 | Shaffer et al. | |
| 5,059,193 A | 10/1991 | Kuslich | |
| 5,098,381 A | 3/1992 | Schneider | |
| 5,108,404 A | 4/1992 | Scholten et al. | |
| 5,176,692 A | 1/1993 | Wilk et al. | |
| 5,192,326 A | 3/1993 | Bao et al. | |
| 5,352,199 A | 10/1994 | Tower | |
| 5,390,683 A | 2/1995 | Pisharodi | |
| 5,411,475 A | 5/1995 | Atala et al. | |
| 5,443,496 A | 8/1995 | Schwartz et al. | |
| 5,514,092 A | 5/1996 | Forman et al. | |
| 5,549,679 A | 8/1996 | Kuslich | |
| 5,571,189 A | 11/1996 | Kuslich | |
| 5,599,301 A | 2/1997 | Jacobs et al. | |
| 5,601,593 A | 2/1997 | Freitag | |
| 5,674,295 A | 10/1997 | Ray et al. | |
| 5,693,100 A | 12/1997 | Pisharodi | |
| 5,707,390 A | 1/1998 | Bonutti | |
| 5,759,191 A | 6/1998 | Barbere | |
| 5,800,392 A | 9/1998 | Racchini | |
| 5,827,289 A | 10/1998 | Reiley et al. | |
| 5,830,228 A | 11/1998 | Knapp et al. | |
| 5,893,850 A | 4/1999 | Cachia | |
| 5,972,015 A | 10/1999 | Scribner et al. | |
| 5,993,484 A | 11/1999 | Shmulewitz | |
| 5,997,582 A | 12/1999 | Weiss | |
| 6,096,038 A | 8/2000 | Michelson | |
| 6,127,597 A | 10/2000 | Beyar et al. | |
| 6,179,856 B1 | 1/2001 | Barbere | |
| 6,235,043 B1 | 5/2001 | Reiley et al. | |
| 6,241,734 B1 | 6/2001 | Scribner et al. | |
| 6,248,110 B1 | 6/2001 | Reiley et al. | |
| 6,293,960 B1 | 9/2001 | Ken | |
| 6,306,177 B1 | 10/2001 | Felt et al. | |
| 6,395,032 B1 | 5/2002 | Gauchet | |
| 6,402,784 B1 | 6/2002 | Wardlaw | |
| 6,425,923 B1 | 7/2002 | Stalcup et al. | |
| 6,440,138 B1 | 8/2002 | Reiley et al. | |
| 6,478,800 B1 | 11/2002 | Fraser et al. | |
| 6,547,804 B2 | 4/2003 | Porter et al. | |
| 6,558,390 B2 | 5/2003 | Cragg | |
| 6,565,606 B1 | 5/2003 | Bruce et al. | |
| 6,607,544 B1 | 8/2003 | Boucher et al. | |
| 6,613,054 B2 | 9/2003 | Scribner et al. | |
| 6,620,162 B2 | 9/2003 | Kuslich et al. | |
| 6,632,235 B2 | 10/2003 | Weikel et al. | |
| 6,638,246 B1 | 10/2003 | Naimark et al. | |
| 6,663,647 B2 | 12/2003 | Reiley et al. | |
| 6,679,886 B2 | 1/2004 | Weikel et al. | |
| 6,706,069 B2 | 3/2004 | Berger | |
| 6,716,216 B1 | 4/2004 | Boucher et al. | |
| 6,719,761 B1 | 4/2004 | Reiley et al. | |
| 6,726,691 B2 | 4/2004 | Osorio et al. | |
| 6,733,532 B1 | 5/2004 | Gauchet et al. | |
| 6,736,793 B2 | 5/2004 | Meyer et al. | |
| 6,740,093 B2 | 5/2004 | Hochschuler et al. | |
| 6,852,095 B1 | 2/2005 | Ray | |
| 6,855,153 B2 | 2/2005 | Saadat | |
| 6,863,672 B2 | 3/2005 | Reiley et al. | |
| 6,899,719 B2 | 5/2005 | Reiley et al. | |
| 6,969,404 B2 | 11/2005 | Ferree | |
| 6,981,981 B2 | 1/2006 | Reiley et al. | |
| 7,001,431 B2 | 2/2006 | Bao et al. | |
| 7,011,684 B2 | 3/2006 | Eckman | |
| 7,025,771 B2 | 4/2006 | Kuslich et al. | |
| 7,044,954 B2 | 5/2006 | Reiley et al. | |
| 7,097,648 B1 | 8/2006 | Globerman et al. | |
| 7,153,307 B2 | 12/2006 | Scribner et al. | |
| 7,166,121 B2 | 1/2007 | Reiley et al. | |
| 7,175,627 B2 | 2/2007 | Lin et al. | |
| 7,175,628 B2 | 2/2007 | Lin et al. | |
| 7,175,629 B2 | 2/2007 | Lin et al. | |
| 7,226,481 B2 | 6/2007 | Kuslich | |
| 7,241,303 B2 | 7/2007 | Reiss et al. | |
| 7,261,720 B2* | 8/2007 | Stevens et al. | 606/105 |
| 7,338,511 B2 | 3/2008 | Mirigian et al. | |
| 7,655,010 B2 | 2/2010 | Serhan et al. | |
| 7,695,488 B2 | 4/2010 | Berenstein et al. | |
| 7,699,894 B2* | 4/2010 | O'Neil et al. | 623/17.12 |
| 7,931,689 B2 | 4/2011 | Hochschuler et al. | |
| 8,043,381 B2 | 10/2011 | Hestad et al. | |
| 8,057,528 B2 | 11/2011 | Parker | |
| 8,147,517 B2* | 4/2012 | Trieu et al. | 606/248 |
| 8,167,944 B2* | 5/2012 | Kim | 623/17.11 |
| 8,460,333 B2* | 6/2013 | Boyle et al. | 606/192 |
| 8,518,115 B2* | 8/2013 | Chavatte et al. | 623/17.12 |
| 2002/0058947 A1 | 5/2002 | Hochschuler et al. | |
| 2002/0068974 A1 | 6/2002 | Kuslich et al. | |
| 2003/0187473 A1 | 10/2003 | Berenstein et al. | |
| 2003/0220649 A1 | 11/2003 | Bao et al. | |
| 2003/0220666 A1 | 11/2003 | Mirigian et al. | |
| 2004/0073308 A1 | 4/2004 | Kuslich et al. | |
| 2004/0097930 A1 | 5/2004 | Justis et al. | |
| 2004/0098017 A1 | 5/2004 | Saab et al. | |
| 2004/0102774 A1 | 5/2004 | Trieu | |
| 2004/0143288 A1 | 7/2004 | Searle | |
| 2004/0167561 A1* | 8/2004 | Boucher et al. | 606/191 |
| 2004/0167625 A1 | 8/2004 | Beyar et al. | |
| 2004/0210297 A1 | 10/2004 | Lin et al. | |
| 2004/0215343 A1 | 10/2004 | Hochschuler et al. | |
| 2004/0215344 A1 | 10/2004 | Hochschuler et al. | |
| 2004/0220615 A1 | 11/2004 | Lin et al. | |
| 2005/0010297 A1 | 1/2005 | Watson et al. | |
| 2005/0070911 A1 | 3/2005 | Carrison et al. | |
| 2005/0143827 A1 | 6/2005 | Globerman et al. | |
| 2005/0209595 A1 | 9/2005 | Karmon | |
| 2005/0209629 A1 | 9/2005 | Kerr et al. | |
| 2005/0234498 A1 | 10/2005 | Gronemeyer et al. | |
| 2005/0273049 A1 | 12/2005 | Krulevitch et al. | |
| 2006/0009844 A1 | 1/2006 | Bloemer et al. | |
| 2006/0079905 A1 | 4/2006 | Beyar et al. | |
| 2006/0100706 A1 | 5/2006 | Shadduck et al. | |
| 2006/0106459 A1 | 5/2006 | Truckai et al. | |
| 2006/0149379 A1 | 7/2006 | Kuslich et al. | |
| 2006/0155296 A1 | 7/2006 | Richter | |
| 2006/0173464 A1 | 8/2006 | Ellman et al. | |
| 2006/0182780 A1 | 8/2006 | Riley et al. | |
| 2006/0190083 A1 | 8/2006 | Arnin et al. | |
| 2006/0217736 A1 | 9/2006 | Kaneko et al. | |
| 2006/0229625 A1 | 10/2006 | Truckai et al. | |
| 2006/0235425 A1 | 10/2006 | Lin et al. | |
| 2006/0271061 A1 | 11/2006 | Beyar et al. | |
| 2006/0293750 A1 | 12/2006 | Sherman et al. | |
| 2007/0055266 A1 | 3/2007 | Osorio et al. | |
| 2007/0055267 A1 | 3/2007 | Osorio et al. | |
| 2007/0055280 A1 | 3/2007 | Osorio et al. | |
| 2007/0055284 A1 | 3/2007 | Osorio et al. | |
| 2007/0055285 A1 | 3/2007 | Osorio et al. | |
| 2007/0093899 A1 | 4/2007 | Dutoit et al. | |
| 2007/0156251 A1 | 7/2007 | Karmon | |
| 2007/0168031 A1 | 7/2007 | Hudgins et al. | |
| 2007/0213760 A1 | 9/2007 | Hayes et al. | |
| 2007/0219490 A1 | 9/2007 | Pepper et al. | |
| 2007/0233258 A1 | 10/2007 | Hestad et al. | |
| 2007/0282443 A1 | 12/2007 | Globerman et al. | |
| 2008/0027546 A1 | 1/2008 | Semler et al. | |
| 2008/0086133 A1 | 4/2008 | Kuslich et al. | |

(56) References Cited

U.S. PATENT DOCUMENTS

| | | |
|---|---|---|
| 2008/0108860 A1 | 5/2008 | Bell et al. |
| 2009/0069850 A1 | 3/2009 | Fuerderer |
| 2009/0182427 A1* | 7/2009 | Liu et al. .................. 623/16.11 |
| 2010/0262240 A1 | 10/2010 | Chavatte et al. |

FOREIGN PATENT DOCUMENTS

| | | |
|---|---|---|
| CA | 2296695 A1 | 2/1999 |
| CN | 1276711 A | 12/2000 |
| DE | 69534156 T2 | 9/2005 |
| DE | 69535492 T2 | 9/2007 |
| EP | 0493789 | 12/1991 |
| EP | 0 338 979 B1 | 8/1992 |
| EP | 0872257 | 4/1997 |
| EP | 1 463 464 B1 | 6/2007 |
| EP | 2 108 323 A2 | 10/2009 |
| EP | 1 459 689 B3 | 11/2009 |
| EP | 1 408 888 B1 | 3/2010 |
| EP | 1 938 765 B1 | 7/2010 |
| EP | 1 104 260 B2 | 6/2013 |
| ES | 2287635 T3 | 12/2007 |
| ES | 2341641 13 | 6/2010 |
| ES | 2348199 T3 | 12/2010 |
| WO | 9505209 | 2/1995 |
| WO | 96/04952 A1 | 2/1996 |
| WO | 98/20939 A2 | 5/1998 |
| WO | 9856301 | 12/1998 |
| WO | 99/02214 A1 | 1/1999 |
| WO | 99/08616 A1 | 2/1999 |
| WO | 0176514 | 10/2001 |
| WO | 0243628 | 6/2002 |
| WO | 03007853 | 1/2003 |
| WO | 2005048856 | 6/2005 |
| WO | 2006034396 | 3/2006 |
| WO | 2006/074410 A2 | 7/2006 |

OTHER PUBLICATIONS

International Search Report and Written Opinion, mailed Jun. 15, 2009, for PCT International Application No. PCT/US2008/083350, filed Nov. 13, 2008.

Saab, Mark A., "Applications of High-Pressure Balloons in the Medical Device Industry" 1999.

Jensen, Mary E., et al., "Percutaneous Polymethylmethacrylate Vertebroplasty in the Treatment of Osteoporotic Vertebral Body Compression Fractures: Technical Aspects"., AJNR: 18, Nov. 1997.

Gangi, Afshin, et al., "Percutaneous Verteroplasty Guided by a Combination of CT and Fluoroscopy"., AJNR 1583-86, Jan. 1994.

Cotten, Anne., MD., et al. "Percutaneous Vertebroplasty for Osteolytic Metastases and Myeloma: Effects of the Percentage of Lesion Filling and the leakage of Methyl Methacrylate at Clinical Follow-up"., Radiology 1996; 200:525-530.

Cotten, Anne, et al., "Preoperative Percutaneous Injection of Methyl Methacrylate and N-Butyl Cyanoacrylate in Vertebral Hemangiomas"; AJNR 17:137-142 (1996).

[No Author Listed] Microporous PTA Balloon Catheter. Match-35™ with microporous drug delivery balloon.Schneider (Europe) AG. 1994, 1 page.

International Preliminary Report on Patentability for Application No. PCT/US2008/083350, mailed May 27, 2010 (10 pages).

* cited by examiner

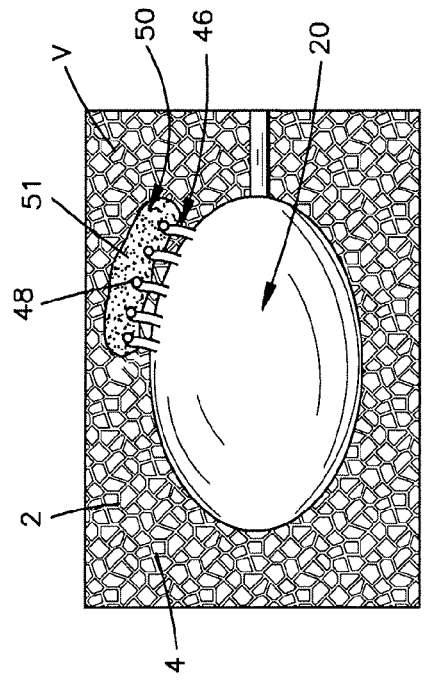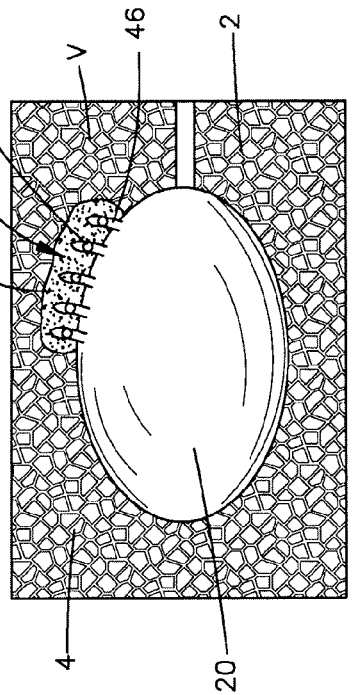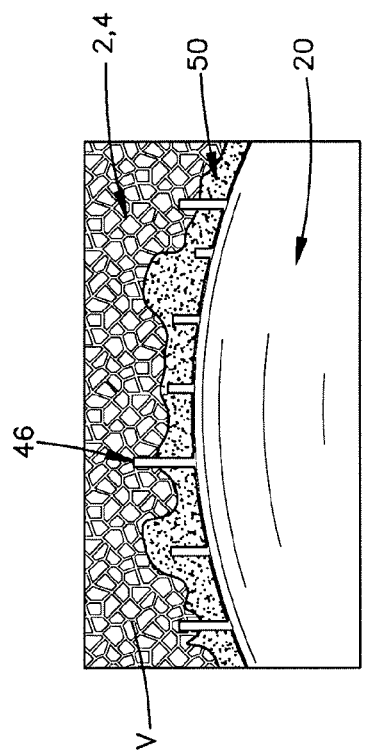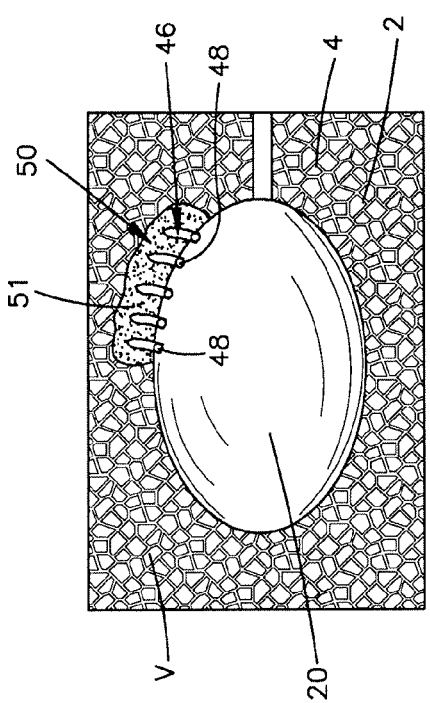

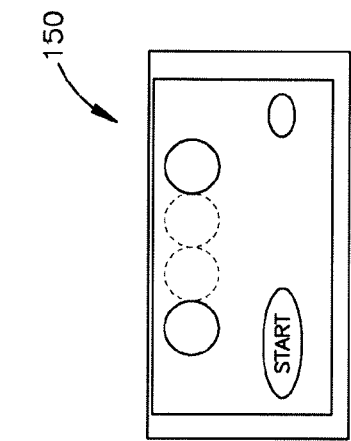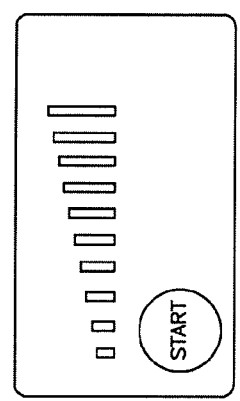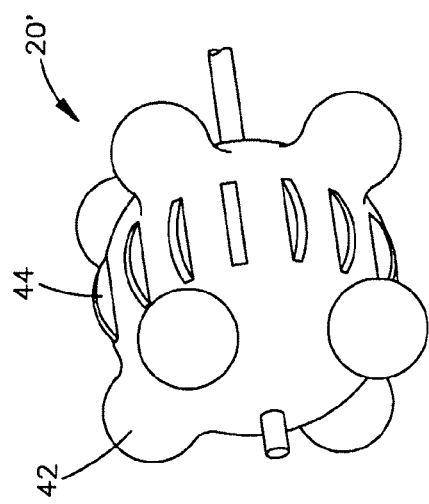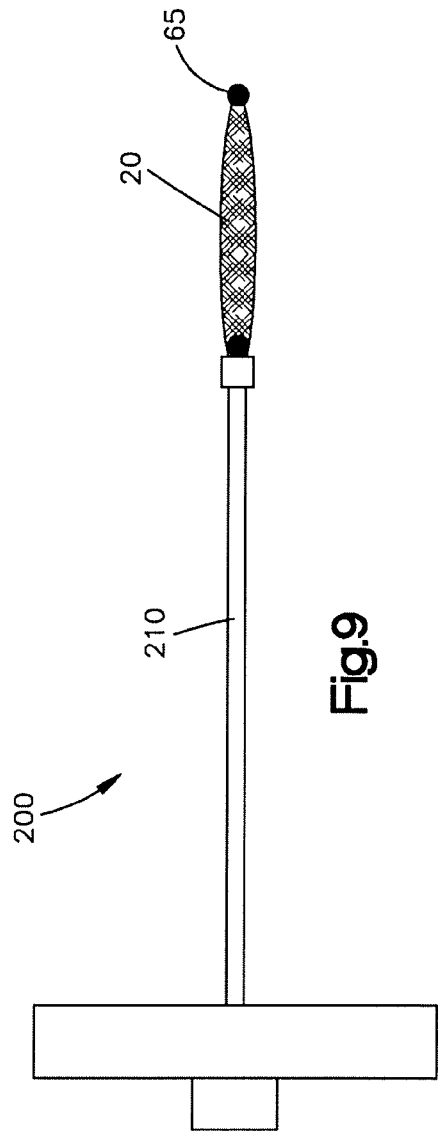

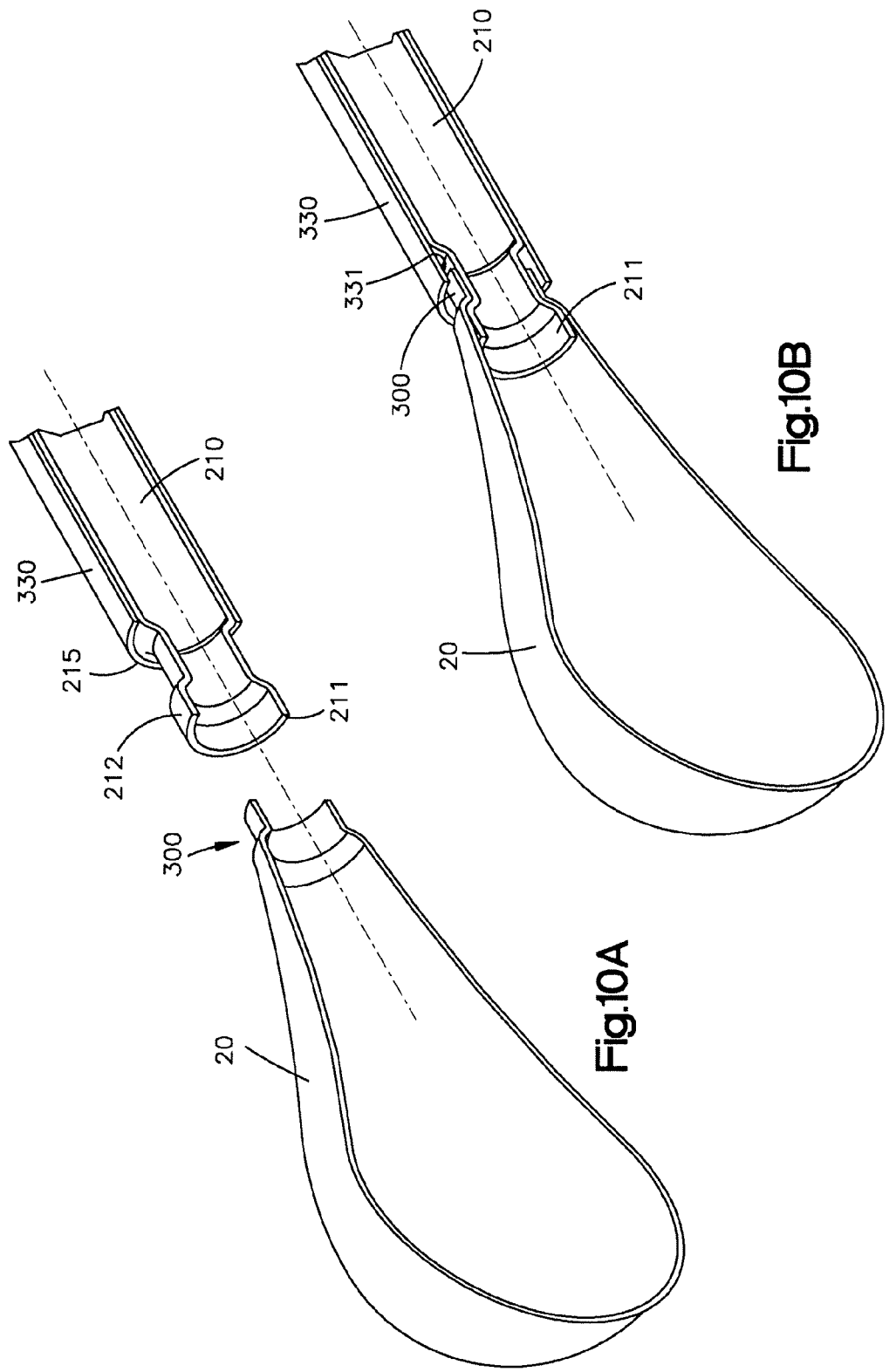

POROUS CONTAINMENT DEVICE AND ASSOCIATED METHOD FOR STABILIZATION OF VERTEBRAL COMPRESSION FRACTURES

CROSS REFERENCE TO RELATED APPLICATIONS

This application is a continuation of U.S. application Ser. No. 12/743,293 filed May 17, 2010, which is a U.S. National Phase Application of International Application No. PCT/US2008/083350 filed Nov. 13, 2008, which claims the benefit of U.S. Provisional Application No. 60/988,696, filed on Nov. 16, 2007, the contents of all prior applications are hereby incorporated by reference in their entirety for all purposes.

FIELD OF THE INVENTION

The present invention relates generally to an implant for augmenting or supporting bones or other structures such as, for example, a vertebral body. More specifically, the present invention relates to a porous or permeable containment device and associated methods and instrumentation for the treatment of compressed bone voids, more specifically, vertebral compression fractures.

BACKGROUND OF THE INVENTION

Vertebral compression fractures ("VCF") represent a common spinal injury and may result in prolonged disability. Generally speaking, VCF involves collapsing of one or more vertebral bodies in the spine. VCF usually occurs in the lower vertebrae of the thoracic spine or the upper vertebrae of the lumbar spine. VCF generally involves fracture of the anterior portion of the affected vertebral body. VCF may result in deformation of the normal alignment or curvature, e.g., lordosis, of the vertebral bodies in the affected area of the spine. VCF and/or related spinal deformities may result, for example, from metastatic diseases of the spine, from trauma or may be associated with osteoporosis. Until recently, doctors were limited in how they could treat VCF and related deformities.

Recently, minimally invasive surgical procedures for treating VCF have been developed. These procedures generally involve the use of a cannula or other access tool inserted into the posterior of the targeted vertebral body, usually through the pedicles.

In one such procedure, a cannula or bone needle is passed through the soft tissue of the patient's back. Once properly positioned, a small amount of polymethylmethacrylate (PMMA) or other orthopedic bone cement is pushed through the needle into the targeted vertebral body. This technique may be effective in the reduction or elimination of fracture pain, prevention of further collapse, and a return to mobility in patients. However, this technique typically does not reposition the fractured bone into its original size and/or shape and, therefore, may not address the problem of spinal deformity due to the fracture.

Other treatments for VCF generally involve two phases: (1) reposition or restoration of the original height of the vertebral body and consequent lordotic correction of the spinal curvature; and (2) augmentation or addition of material to support or strengthen the fractured or collapsed vertebral body.

One such treatment involves inserting, through a cannula, a catheter having an expandable member into an interior volume of a fractured vertebral body, wherein the interior volume has a relatively soft cancellous bone surrounded by fractured cortical bone therein. The expandable member is expanded within the interior volume in an attempt to restore the vertebral body towards its original height. The expandable member is removed from the interior volume, leaving a void within the vertebral body. PMMA or other bone filler material is injected through the cannula into the void to stabilize the vertebral body. The cannula is then removed and the cement cures to augment, fill or fix the vertebral body.

Another approach for treating VCF involves inserting an expandable mesh graft balloon or containment device into the targeted vertebral body. The graft balloon remains inside the vertebral body after it is inflated with PMMA or an allograft product, which limits intra-operative loss of height of the repositioned endplates.

It is desirable in the art to provide a safe and effective porous or permeable containment device and methods for aiding and/or augmenting fractured or otherwise damaged vertebral bodies and other bones, preferably a porous or permeable containment device that may be inserted via a minimally invasive surgical technique and which prevents slippage between the containment device and the surrounding bone tissue.

SUMMARY OF THE INVENTION

The present invention is directed to a porous or permeable containment device for implanting into an interior volume of a targeted vertebral body for use in restoring the anatomy of the targeted vertebral body. The containment device is expandable from an insertion configuration to an expanded configuration via, for example, a bone filler material such as, for example, a bone cement. Expansion of the containment device by injection of the bone filler material preferably facilitates (i) cavity creation within the interior volume of the targeted vertebral body, (ii) height restoration of the vertebral body, (iii) filling of the cavity formed in the interior volume of the targeted vertebral body, and (iv) stabilization, aiding and/or augmentation of the targeted vertebral body. The porous or permeable containment device preferably enables (i) controlled bone cement outflow, (ii) increased contact surface with the surrounding cancellous bone and (iii) stabilization of the rotational and axial-translational movements of the porous containment device with respect to the surrounding cancellous bone.

The containment device preferably permits the bone filler material to flow out of or through the outer surface of the containment device via, for example, one or more pores formed in the outer surface, one or more flow-directing tentacles extending from the outer surface, by forming the containment device from a permeable material, etc. so that the bone filler material may interdigitate with the surrounding bone tissue. The containment device is preferably configured to have a pre-determined, specific shape such as, for example, a "dog-bone" or "dumb-bell" shape, when in the expanded configuration, in order to enhance primary stabilization. The pores may also incorporate a specific shape and configuration to optimally meet the requirements of secreting the bone filler material, tissue infiltration and anchorage of the containment device to the surrounding bone tissue.

The containment device preferably also includes one or more knobs or ribs to facilitate anchoring of the containment device to the surrounding bone tissue, one or more air or fluid evacuation pores to permit air or fluid from escaping from the interior volume of the containment device, one or more radiopacity rings or markers to enable a surgeon to locate and/or position the containment device under X-ray imaging, and/or any of the other features disclosed herein.

BRIEF DESCRIPTION OF THE DRAWINGS

The foregoing summary, as well as the following detailed description of the preferred embodiments of the application, will be better understood when read in conjunction with the appended drawings. For the purposes of illustrating the porous containment device of the present application, there is shown in the drawings preferred embodiments. It should be understood, however, that the application is not limited to the precise arrangements and instrumentalities shown. In the drawings:

FIG. 5 illustrates a detailed, partial view of an alternate exemplary embodiment of a containment device incorporating a plurality of tentacles extending from an outer surface of the containment device in accordance with one aspect of the present invention;

FIG. 6A illustrates a detailed, partial view of the containment device shown in FIG. 5 being expanded by bone filler material;

FIG. 6B illustrates a detailed, partial view of the containment device shown in FIG. 5 being further expanded by bone filler material;

FIG. 6C illustrates a detailed, partial view of the containment device shown in FIG. 5 being further expanded by bone filler material;

FIG. 7 illustrates an alternate exemplary embodiment of a containment device, the containment device including a plurality of knobs and ribs in accordance with one aspect of the present invention;

FIG. 8A illustrates an exemplary embodiment of a cement viscosity indicator in accordance with another aspect of the present invention;

FIG. 8B illustrates an alternate, exemplary embodiment of a cement viscosity indicator;

FIG. 9 illustrates a side view of an exemplary embodiment of a cannulated sleeve used in connection with the porous containment device of the present invention;

FIG. 10A illustrates an exploded, perspective view of an exemplary coupling mechanism for coupling the porous containment device to a cannulated sleeve; and FIG. 10B illustrates a perspective view of the porous containment device coupled to the cannulated sleeve device via the coupling mechanism illustrated in FIG. 10A.

DETAILED DESCRIPTION OF THE INVENTION

Figure 1A:
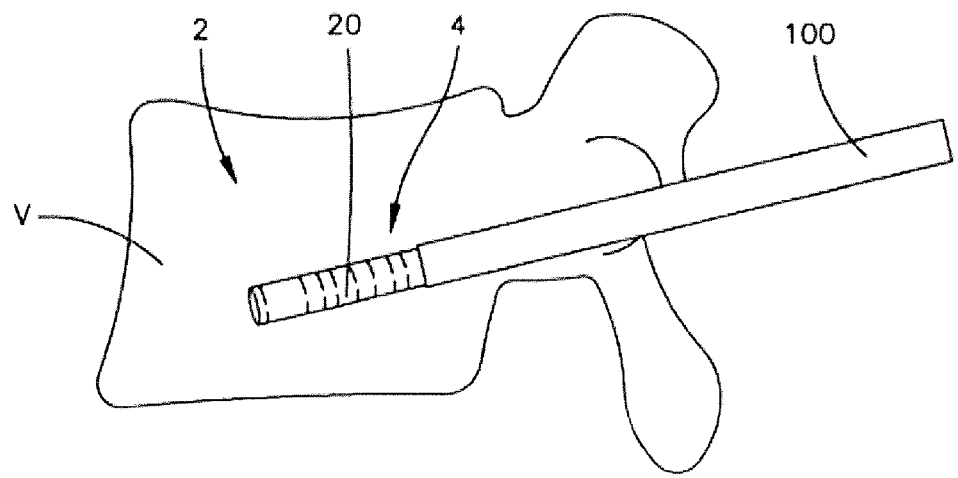
FIG. 1A illustrates an exemplary embodiment of a containment device inserted into an interior volume of a targeted vertebral body, the containment device illustrated in an insertion configuration.
Figure 1B:
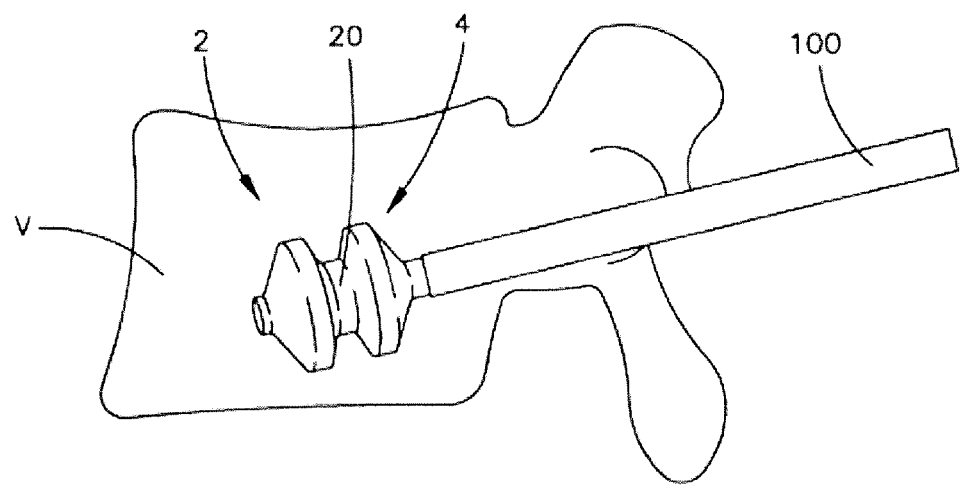
FIG. 1B illustrates the containment device shown in FIG. 1A in an expanded configuration.

Certain terminology is used in the following description for convenience only and is not limiting. The words "right", "left", "lower", "upper", "top" and "bottom" designate directions in the drawings to which reference is made. The words "inwardly" and "outwardly" refer to directions toward and away from, respectively, the geometric center of the device and designated parts thereof. The words, "anterior", "posterior", "superior", "inferior" and related words and/or phrases designate preferred positions and orientations in the human body or with respect to the implant of the present application to which reference is made and are not meant to be limiting. The terminology includes the above-listed words, derivatives thereof and words of similar import.

Certain exemplary embodiments will now be described with reference to the drawings. In general, such embodiments relate to an implant for creating a cavity within an interior volume of a vertebral body, for restoring the height of the vertebral body, for filling the cavity formed in the vertebral body and for stabilizing, aiding and/or augmenting the patient's vertebral body and spine. As generally understood by one of ordinary skill in the art, it should be understood that while the preferred implant will be described as and may generally be used in the spine (for example, in the lumbar, thoracic or cervical regions), those skilled in the art will appreciate that the implant may be used in other parts of the body such as, for example, long bones or bones in the hand, face, feet, extremities, cranium, or in nearly any bone in the human body.

Figure 2A:
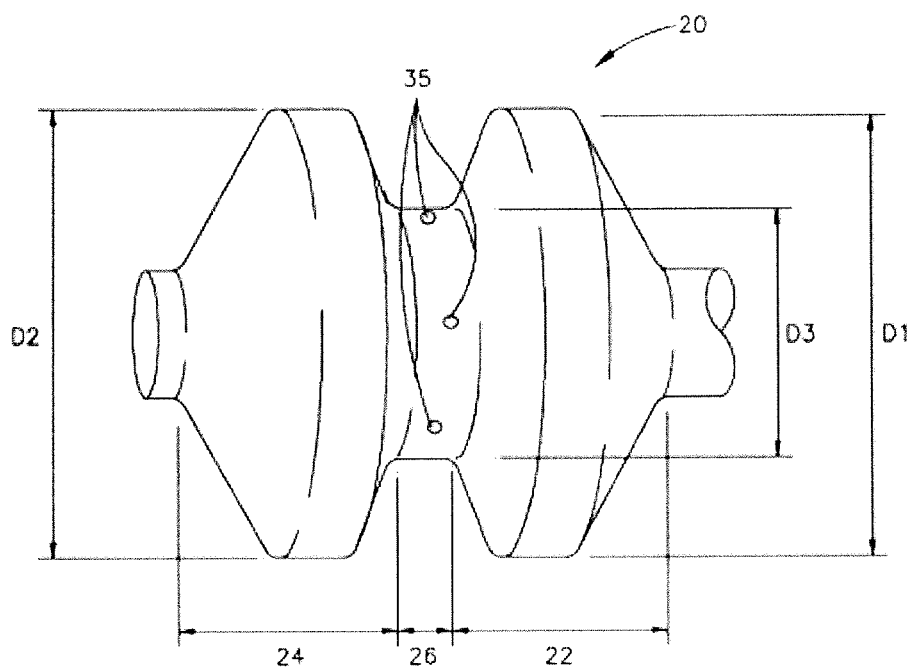
FIG. 2A illustrates a perspective view of an exemplary embodiment of a containment device in accordance with one aspect of the present invention.
Figure 2B:
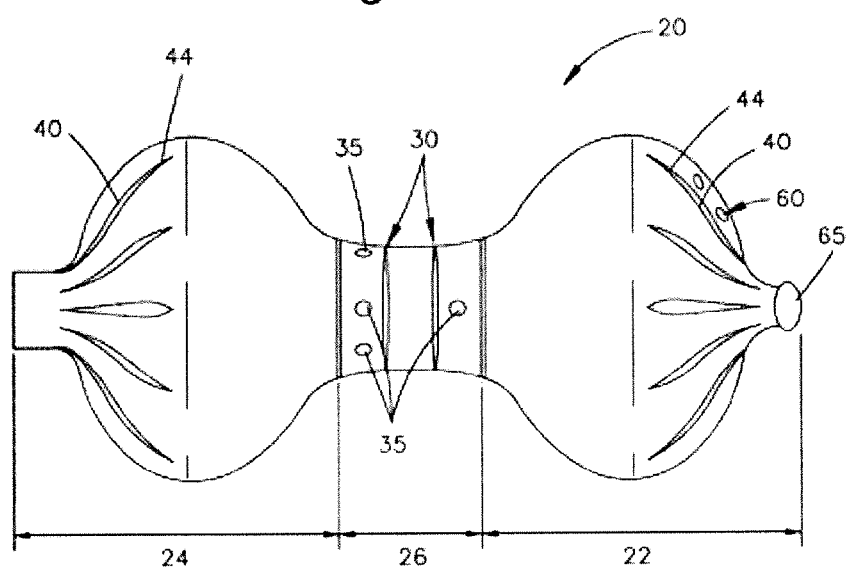
FIG. 2B illustrates a side view of the containment device shown in FIG. 2A, the containment device illustrating different exemplary features not illustrated in FIG. 2A.
Figure 3:
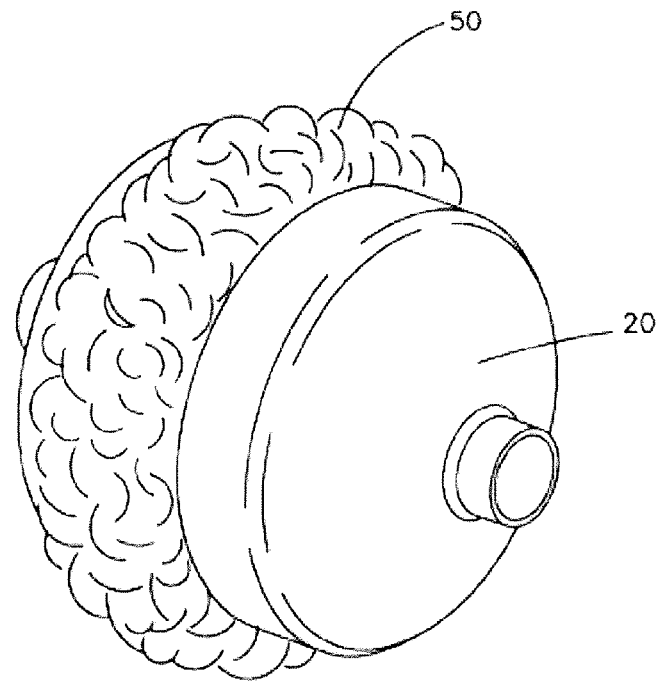
FIG. 3 illustrates an alternate perspective view of the containment device shown in FIG. 2A, the containment device including secreted bone filler material semi-contained between enlarged distal and proximal portions of the device in accordance with one aspect of the present invention.
Figure 4:
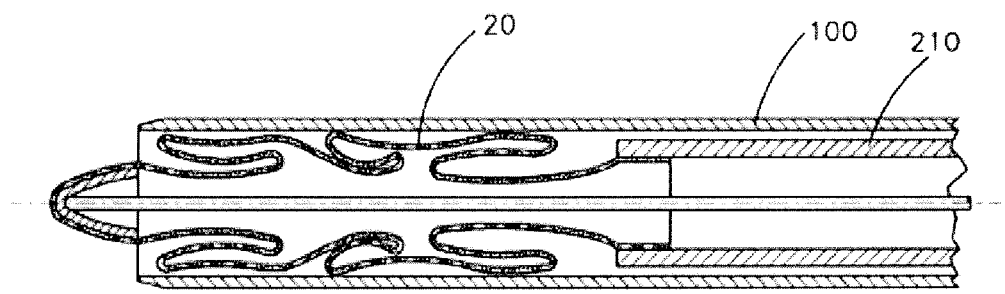
FIG. 4 illustrates a side view of the containment device in an insertion configuration within the lumen of a cannula.

Referring generally to FIGS. 1A-7, the present invention is generally directed to a porous or permeable containment device 20 (collectively referred to herein as a "porous containment device" and/or a "containment device") and to a system and method for inserting the porous containment device 20 into a targeted vertebral body V of a vertebra, such as, for example, one which has been subjected to a VCF. The porous containment device 20 is preferably sized and configured to be inserted into an interior volume 2 of the targeted vertebral body V via a minimally invasive surgical technique, such as, for example, through one or more cannulas 100 (as best shown in FIG. 4), preformed holes or percutaneously. Once inserted into the interior volume 2 of the targeted vertebral body V, the porous containment device 20 is expandable from an insertion configuration (as best shown in FIGS. 1A and 4) to an expanded configuration (as best shown in FIGS. 1B, 2A, 2B, 3 and 7) so that the porous containment device 20 may generally create a cavity within the interior volume 2 of the targeted vertebral body V, restore the height of the vertebral body V and stabilize, aid and/or augment the interior volume 2 of the targeted vertebral body V. Preferably, the porous containment device 20 is capable of repositioning and stabilizing the targeted vertebral body V to re-establish structural integrity and avoid painful micro-movements.

The porous containment device 20 is preferably expanded from the insertion configuration to the expanded configuration via a bone filler material 50. The bone filler material 50 may be, for example, bone chips, allograft bone or any other filling material now or hereafter known in the art. Preferably the bone filler material is a biocompatible bone cement such as, for example, polymethylmethacrylate (PMMA) that is self hardening (e.g., self-curing) and that is capable of interdigitating with the surrounding bone tissue 4 found in the interior volume 2 of the targeted vertebral body V. In this manner, the filling of the cavity formed in the vertebral body and the stabilization of the targeted vertebral body V is accomplished by the injection of the bone filler material 50, the expansion of the porous containment device 20 and the controlled secretion of the bone filler material 50 out of or through the porous containment device 20, as will be described in greater detail below.

In use, the porous containment device 20 is inserted preferably via a minimally invasively apparatus or system 100 into a targeted vertebral body V. The porous containment device 20 is preferably then expanded from the insertion configuration to the expanded configuration via injection of the bone filler material 50 into the inner cavity of the porous containment device 20 using an injection device. The expansion of the porous containment device 20 preferably compresses the surrounding cancellous bone tissue 4 in the interior volume 2 of the targeted vertebral body V thereby forming a cavity. Expansion of the porous containment device 20 also preferably repositions and stabilizes the surrounding bone and/or bone tissue 4. That is, the porous containment device 20, in the expanded configuration, is preferably structurally strong enough to impart a force to the surrounding bone tissue 4 in the interior volume 2 of the targeted vertebral body V sufficient to restore the anatomical alignment of the fracture vertebral body V until hardening of the injected bone filler material 50.

The outer surface of the porous containment device 20 is preferably configured so that a small amount of bone filler material 50 is secreted, more preferably directionally secreted, out of or through the porous containment device 20. The relatively small amount of bone filler material 50 may be secreted out of or through the porous containment device 20 via one or more pores 35 formed in the containment device 20, by one or more tentacles 46 extending from the outer surface of the containment device 20, by forming the porous containment device 20 from a permeable material, etc. Once secreted, the bone filler material 50 cures to form a cement layer 51 around the porous containment device 20 that interdigitates with the surrounding bone tissue 4 (resulting in a layer of cement-bone compound 51). The porous containment device 20, once filled with the bone filler material 50, remains within the interior volume 2 of the targeted vertebral body V to preferably assist in load bearing and structural support of the vertebral body V as the bone filler material 50 cures.

The porous containment device 20 may be configured so as to be semi-constrained or selectively reinforced. In this manner, the porous containment device 20 may be configured so that in the expanded configuration, the containment device 20 has a pre-determined size and shape. For example, the porous containment device 20 may be configured to expand in one direction but not in another, e.g., preferably radially rather than in length. Alternatively or in addition, the porous containment device 20 may be configured to expand towards an area of less resistance. The porous containment device 20 may be configured so that in the expanded configuration, the device has, for example, a cylindrical, conical, cigar-like, rounded, or other desired shape.

In a particularly preferred embodiment and as generally shown in FIGS. 2A, 2B and 3, the porous containment device 20 may be in the form of an expandable balloon that, when in the expanded configuration, has a "dog-bone" or "dumb-bell" type shape (collectively referred to herein as a "dog-bone"). That is, the porous containment device 20 includes a proximal portion 22 having an outer diameter D1, a distal portion 24 having an outer diameter D2, and a central portion 26, located between the proximal and distal portions 22, 24, having an outer diameter D3. The diameter D3 of the central portion 26 is less than the diameters D1 and D2 of the proximal and distal portions 22, 24, respectively, thus forming the "dog-bone" shape. Diameter D1 may be equal to, larger than or smaller than diameter D2. Moreover, it is envisioned that the narrower diameter D3 can be located in the proximal or distal portions 22, 24 of the porous containment device 20. Diameter D3 preferably is approximately 5% to 60% of the diameter D1 and/or D2 to enable the enlarged diameter distal and proximal portions 22, 24 to act as a buffer and to allow for a pooling effect or to substantially semi-contain the secreted bone filler material 50, as will be described in greater detail below. By providing enlarged distal and proximal end portions 22, 24, the containment device 20 facilitates better interdigitation with the surrounding bone tissue 4. In addition, the containment device 20 enables 360 degrees of secreted bone filler material 50 for interdigitation with the surrounding bone tissue 4 (as best illustrated in FIG. 3).

It should be further noted that it is envisioned that the containment device 20 may include a plurality of narrower portions. For example, the containment device 20 may include two narrower portions sandwiched between three enlarged diameter portions such that the containment device 20 may have a double, "dog-bone" shape.

The "dog-bone" shaped porous containment device 20 may be made by incorporating one or more internal or external constraints such as, for example, one or more wires, one or more metal radial rings or any form of supportive yarn 30 to constrain expansion of the narrower diameter central portion 26.

As shown, the "dog-bone" shaped containment device 20 preferably includes a plurality of pores 35 formed in the narrower central portion 26. In this manner, in use, the porous containment device 20 enables outflow of the bone filler material 50 through the plurality of pores 35 formed in the narrower central portion 36 of the porous containment device 20. In the expanded configuration, the enlarged diameter proximal and distal portions 22, 24 act as buffers so that the secreted bone filler material 50 is substantially, semi-contained in the narrower central portion 26 and the secreted bone filler material 50 is thereby pooled or semi-contained in a buffered zone between the enlarged diameter distal and proximal portions 22, 24 (as best illustrated in FIG. 3). The secreted bone filler material 50 preferably forms a cement layer 51 around the porous containment device 20 to facilitate interdigitation of the containment device 20 with the surrounding bone tissue 4.

The plurality of pores 35 located in the narrower central portion 26 are preferably oriented so that the outflow of bone cement 50 is directed centrally and/or towards the base (e.g., towards the outer surface) of the narrower central portion 26. The enlarged distal and proximal portions 22, 24 will act as a buffering system limiting and/or preventing anterior or posterior backflow or leakage.

In one embodiment, the one or more pores 35 may be initially covered with a material or closed by having a locally smaller thickness than that which characterizes the remainder of the porous containment device 20. The pores 35 may include a predetermined breaking point such that the pores 35 rupture or open upon experiencing a certain predetermined pressure.

The number of pores 35 and the diameter of the pores 35 are preferably selected to optimize desired cement outflow. Preferably the "dog-bone" shaped porous containment device 20 includes between one and twenty pores 35 depending on the size of the porous containment device 20. Although larger number of pores 35 may be incorporated. The pores 35 can be positioned anywhere between the midline of the narrower central portion 26 and the walls of the enlarged distal and proximal portions 22, 24. The diameter of the pores 35 is preferably between about 50 microns and about 1,000 microns and more preferably about 450 microns.

Alternatively and/or in addition, the porous containment device 20 may include one or more surface enhancing structures 40 to improve the frictional contact strength of the porous containment device 20 with the surrounding bone tissue 4 found in the interior volume 2 of the targeted vertebral body V thereby helping to further anchor and to prevent slippage of the porous containment device 20 within the targeted vertebral body V.

The surface enhancing structures 40 may be in the form of knobs 42 or ribs 44. For example, the porous containment device 20 may include a plurality of axial or longitudinal ribs, radial or diametric ribs, C-shaped ribs, T-shaped ribs, etc. In addition to help facilitate anchoring the containment device 20 to the surrounding bone tissue 4, the surface enhancing structures 40 may also be positioned relative to the plurality of pores 35 to help direct the outflow of the bone filler material 50. That is, the surface enhancing structures 40 may be placed on or formed on the containment device 20 to help direct the outflow of the bone filler material 50. For example, one or more pores 35 may be placed between adjacent ribs 44 so that any secreted bone filler material 50 may be contained by the adjacent ribs 44. In addition, the placement of the ribs 44 may be used to direct the flow of the bone filler material 50 such as, for example, to direct the flow of the bone filler material 50 so that it only flows in the anterior-posterior direction, etc.

Alternatively and/or in addition, the porous containment device 20 may include a plurality of projections (not shown) having, for example, a donut or red-blood cell shaped structure. That is, the porous containment device 20 may include a plurality of circular projections with a central hole wherein each projection surrounds a pore 35 so that as the bone filler material 50 is secreted from the pore 35, the secreted bone filler material 50 is substantially contained by and remains within the central hole formed in the donut shaped projection.

Alternatively and/or in addition, the surface enhancing structures 40 may be in the form of tentacles 46 (as best shown in FIGS. 5-6C). That is, in order to facilitate primary fixation of the surrounding bone tissue 4 with the outer surface of the porous containment device 20, the outer surface of the porous containment device 20 may include a plurality of tentacles 46, which are projections extending from the outer surface of the porous containment device 20. The arrangement of the tentacles 46 can assume many different forms and may be tailored to the requirements of the surgery and the specific anatomy of the patient and may, for example, be arranged homogenously or non-homogenously about the outer surface of the porous containment device 20. Alternatively, the plurality of tentacles 46 may be arranged only on one or more surfaces such as, for example, only on the superior and inferior surfaces, of the porous containment device 20 (e.g., the surfaces that face the top and bottom interior endplates of the vertebral body) or on the superior and inferior surfaces but unilaterally arranged.

Each of the plurality of tentacles 46 preferably includes one or more openings 48 at the outer end or tip thereof for directing the outflow of the bone filler material 50 to form a cement layer 51 around the porous containment device 20 to facilitate interdigitation of the containment device 20 with the surrounding bone tissue 4 in the interior volume 2 of the targeted vertebral body V (as best shown in FIG. 6A). Alternatively, the one or more openings 48 may be formed at the foot of the tentacles 46 (as best shown in FIG. 6B) or between the foot of the tentacles 46 and the outer end or tip of the tentacles 48 (as best shown in FIG. 6C). Moreover, the one or more openings 48 may be formed along the length of the tentacles 46. In one embodiment, the one or more openings 48 may include a predetermined breaking point such that the openings 48, which may be initially covered with a material or closed by having a locally smaller thickness than that which characterizes the remainder of the porous containment device 20, ruptures upon experiencing a certain predetermined pressure.

In addition, in some embodiments, the plurality of tentacles 46 may be sufficiently rigid to assist in anchoring the porous containment device 20 into and/or with the surrounding bone tissue 4 and to prevent shear force delamination between the surrounding bone tissue 4, the bone filler material 50 and the porous containment device 20.

In use, as the porous containment device 20 is expanded via injection of the bone filler material 50 into the inner cavity of the porous containment device 20, the plurality of tentacles 46 formed on the outer surface of the porous containment device 20 preferably extend and/or become adhered with the surrounding bone tissue 4. In addition, the one or more openings 48 formed in the tentacles 46 preferably direct the bone filler material 50 to flow out of the porous containment device 20 and into the surrounding bone tissue 4.

It should be noted that it is envisioned that the one or more surface enhancing structures 40 (e.g., the knobs 42, ribs 44 or tentacles 46) can be used in connection with any known or hereafter developed containment device including, for example, non-porous containment devices. For example, as best shown in FIG. 7, the containment device 20' may be in the form of a rounded or rectangular shaped containment device. The containment device 20' may be porous or non-porous. The containment device 20' including a plurality of knobs 42 and ribs 44 to facilitate anchoring of the containment device 20' to the surrounding bone tissue 4.

Alternatively or in addition, the porous containment 20 device preferably includes one or more air and fluid evacuation pores 60 to enable the bone filling material 50 and any blood or any fluid or air within the inner cavity of the porous containment device 20 to escape. Preferably the one or more air and fluid evacuation pores 60 have a diameter of about 1 micron to about 49 microns.

Alternatively or in addition, the porous containment device 20 preferably includes one or more radiopacity rings or markers 65 to enable the surgeon to precisely locate and/or position the porous containment device 20 under X-ray imaging.

Preferably the bone filler material 50 is secreted from the porous containment device 20 at a pressure different from the injected pressure that expands the porous containment device 20, as will be described in greater detail below.

The size and the total surface area of the pores 35 and/or openings 48 are preferably configured so that only a limited amount of viscous bone filler material 50 can exit from the porous containment device 20 during initial injection of the bone filler material 50. As will be described in greater detail below, initial injection of the bone filler material 50 preferably occurs at a relatively low viscosity. As previously stated, the pores 35 and/or openings 48 can be engineered to include a predetermined breaking point such as, for example, forming the pores 35 and/or openings 48 with a locally thinner material thickness than that of the rest of the porous containment device 20, so that the pores 35 can rupture in response to reaching a predetermined pressure. The interaction between the viscosity of the bone filler material 50 (rather high) and the geometry of the pores 35 and/or openings 48 (rather small) is coordinated to reach a balanced outcome fulfilling the requirements of cavity creation, height restoration, and secretion of the bone filler material 50 locally to infiltrate into the surrounding bone tissue 4.

Thus, in use, in order to facilitate a proper combination of cement-tissue interdigitation with volume or height restoration, the bone filler material 50 may be injected into the porous containment device 20 in a liquid or pasty form, and in a preferred embodiment, a volume of 1-5 cc of bone cement 50 is initially injected into the porous containment device 20 at a low viscosity to allow for controlled extravagation and interdigitation with the surrounding bone tissue 4. Thereafter, additional injection of 1-5 cc of bone cement 50 at a relatively higher viscosity will allow volume creation and thus height restoration and will further enhance the interdigitation of the secreted bone cement 50 with the surrounding bone tissue 4. Preferably the bone cement 50 is initially injected at a low viscosity of between about 30 Pas to about 150 Pas. Thereafter, the bone cement 50 is injected at a relatively higher viscosity between about 300 Pas to about 2,000 Pas.

To facilitate bone cement 50 injection, the system preferably incorporates a single use or multiple use cement viscosity indicator 150 (as best shown in FIGS. 8A and 8B). During bone cement 50 injection, a correct indication of the cement viscosity is important in order to guarantee safe and efficient void filling. Injection of a bone cement 50 with too high of a viscosity or too low of a viscosity might result in bone cement leakage or inappropriate execution of a medical technique. Injection of a bone cement 50 with too high of a viscosity might also result in inappropriate filling of the bone voids, damage to surrounding tissue, etc. Generally speaking however it is difficult for surgeons to know the viscosity of the bone cement 50 at any given time in the surgical operating room.

The cement viscosity indicator 150 includes a processor containing a mathematical algorithm. Preferably, the cement viscosity indicator 150 is a compact sterile electronic device allowing application directly within the surgical operating room thereby allowing accurate reading of the room temperature and thus determination of the bone cement viscosity in time.

In use, upon start up, the cement viscosity indicator 150 measures the current room temperature and runs the temperature through the computer algorithm. Once the algorithm determines that the bone cement 50 is within a predetermined acceptable viscosity, the cement viscosity indicator 150 informs the surgeon that the bone cement 50 is ready for injection. In accordance with the preferred two-step injection method, as previously described, the cement viscosity indicator 150 preferably indicates to the surgeon when the bone cement 50 has achieved the proper low viscosity for initial injection and when the bone cement 50 has achieved the proper high viscosity for final injection.

The cement viscosity indicator 150 may function by registering one or more points in time corresponding with a specific viscosity. This will allow application of bone cement 50 with the right viscosity at the right moment. Obtaining the right viscosity could be communicated under the form of a visual and/or acoustic signal.

The porous containment device 20 preferably has a diameter of about 10 mm to about 25 mm in height and a length of about 10 mm to about 25 mm, when in the expanded configuration. Although other larger or smaller dimensions may be used. The porous containment device 20 may be used as a stand-alone device or in combination with one or more other containment devices in the same interior volume 2 of the targeted vertebral body V such as, for example, in a transpedicular approach.

The porous containment device 20 may be in the form of a balloon. The balloon may be made from any biocompatible material now or hereafter known including but not limited to polycarbonate (PU), polycarbonate urethane (PCU), polyethylene terephthalate (PET), polyethylene (PE), thermoplastic polyamide (TPA), PEBAX, or other elastic and expandable polymeric materials, or inelastic polymer materials. Alternatively, the porous containment device 20 can be in the form of a mesh. The mesh can be made from any biocompatible material now or hereafter known including but not limited to polyetheretherketone (PEEK), polyethylene terephthalate (PET), polycarbonate (PU), etc. Alternatively, the porous containment device 20 can be made from a resorbable material that is preferably naturally resorbed by the human body over time. Forming the porous containment device 20 from a resorbable material is particular useful when using a bone filler material 50 that is naturally replaced by bone over time. The porous containment device 20 can also be formed of a permeable membrane or a mesh-like material that allows the bone filler material 50 to flow out of the outer surface of the containment device 20 and into contact with the surrounding bone tissue 4, with or without the inclusion of pores 35, tentacles 46, etc.

The porous containment device 20 is preferably preformed (e.g., presized and shaped) when in the expanded configuration and is made of a non-elastic or semi-rigid material.

Alternatively or in addition, the porous containment device 20 may be reinforced by or used with a stent, a stent-like structure, a deformable mesh or reinforcing fibers, which may act as both an expansion device and a filler sack, in which most of the bone filler material 50 remains after injection but which permits some bone filler material 50 to escape through the stent or mesh to interdigitate with the surrounding bone tissue 4.

Alternatively or in addition, the porous containment device 20 may be made from a material, which as a result of the rising temperature from the bone filler material 50 curing, undergoes a chemical reaction with the bone cement 50 causing the porous containment device 20 to merge, fuse, melt, or crosslink with the bone cement 50.

Alternatively or in addition, the porous containment device 20 may be made from a material, which as a result of the rising temperature from the bone filler material 50 curing, becomes liquid so that the melted containment device flows into and interacts with the surrounding bone tissue 4. Alternatively, only a portion of the containment device 20 may be configured to melt as a result of the rising temperature from the bone cement 50 curing, such as, for example, only the knobs 42, ribs 44 or tentacles 46.

In an alternate embodiment (not shown), the porous containment device may include an outer containment device and an inner containment device such that the outer containment device surrounds the inner containment device. In use, the inner containment device is responsible for cavity creation and for restoring the high of the vertebral endplates. The outer containment device is responsible for enabling bone filler material to interdigitate with the surrounding bone tissue. The inner containment device may include a plurality of pores that are smaller in diameter or fewer in number than those formed in the outer containment device. The inner containment device and the outer containment device may be simultaneously inserted into the targeted vertebral body in an insertion configuration. Alternatively, the inner and outer containment devices may be inserted sequentially in separate steps.

In use, bone filler material is preferably injected into the inner containment device to facilitate cavity creation and repositioning of the vertebral body without a large out-flow of bone filler material. Bone filler material preferably flows through the inner containment device, more preferably through the pores formed in the inner containment device, and into the area between the inner and outer containment devices eventually resulting in the bone filler material passing through the outer containment device and into engagement with the surrounding bone tissue. The inner containment device may be configured to permit the bone filler material to outflow only after a predetermined pressure or volume is achieved in the inner cavity of the inner porous containment device. The outer porous containment device preferably permits local outflow of bone filler material to thereby form a bone cement layer around at least a portion of the outer porous containment device that interdigitates with surrounding bone tissue to anchor the containment device to the surrounding bone tissue, while at the same time acting a safety barrier for the inner containment device.

Alternatively, the inner containment device may include pores or openings substantially equal in number and/or diameter to those which characterize the surrounding outer containment device, or may include pores or openings greater in number and/or diameter to those which characterize the surrounding outer containment device. The additional material thickness as a result of incorporating an outer containment device reduces the likelihood of damage to the containment device during expansion.

As previously mentioned, the surface enhancing structures 40 (e.g., the knobs 42, ribs 44 or tentacles 46) can be used in connection with a non-porous containment device. One exemplary method of using one or more surface enhancing structures with a non-porous containment device includes compacting the interior volume of the targeted vertebral body using a cavity creation device such as, for example, an inflatable balloon. After removal of the cavity creation device, injecting a limited amount of bone filler material into a cannula or into the interior volume of the targeted vertebral body. Inserting the non-porous containment device having one or more surface enhancing structures formed thereon into the targeted vertebral body. Expanding the non-porous expandable containment device by, for example, injecting a bone filler material into the inner cavity of the non-porous expandable containment device so that the textured outer surface of the non-porous containment device interdigitates with both the layer of bone cement formed by the initial injection of bone filler material into the cannula or into the interior volume of the targeted vertebra body, as well as interdigitates with the surrounding bone tissue. Additional bone filler material may also be injected within the cannula or through the cannula during expansion of the non-porous expandable containment device. The non-porous expandable containment device may then be removed and the cannula may then be filled with a load bearing system which remains within the interior volume to mechanically bear load. The load bearing system may be in the form of a non-porous expandable containment device that is inflated with a self-hardening bone filler material or any other system that can be expandable, cannula filling and load bearing (e.g. an expandable stent-like structure or a bobbin-like structure around which is wound biocompatible yarn-like material that forms an expanded load bearing structure within the cannula). Alternatively, the lastly inserted load bearing system may simply be a bone filler material that fills the created cavity. In order to avoid delamination between the layer of the first bone filler material and the layer of the second bone filler material, the second bone filler material preferably interdigitates with the first bone filler layer via, for example, the openings formed in the layer of the first bone filling material that was created by the textured outer surface such as, for example, via the tentacles, formed on the second expandable container.

As previously mentioned, the bone filler material 50 is preferably injected into the inner cavity of the porous containment device 20 via an injection device 200. The injection device 200 may be any device now or hereafter known for such purpose. Referring to FIG. 9, one exemplary embodiment of an injection device 200 will now be described. As shown, the porous containment device 20 (shown in the insertion configuration) may be detachably coupled to a cannulated sleeve 210. The cannulated sleeve 210 may be coupled to the containment device 20 by any means now or hereafter known in the art for such purpose including, but not limited to, a simple mechanical connection. For example the cannulated sleeve 210 may be coupled to the containment device 20 via a friction fit, a press-fit or a force fit. In this manner, the cannulated sleeve 210 may be coupled to the containment device 20 by pressure and all forces can be transmitted by friction. In use, the containment device 20 can be decoupled from the cannulated sleeve 210 by holding the containment device 20 in place and pulling the cannulated sleeve 210 away from the porous containment device 20. Alternatively, the cannulated sleeve 210 may be coupled to the containment device 20 by a threaded connection, by a bayonet coupling, a plug-in connector such as, by a pin formed in the cannulated sleeve 210 for engaging a slot formed in the containment device 20.

Moreover, the cannulated sleeve 210 may be coupled to the containment device 20 by an intermediary balloon. That is, an intermediary balloon may be formed on the cannulated sleeve 210 adjacent to a distal end thereof. The cannulated sleeve 210 and the intermediary balloon are then inserted into the containment device 20. Thereafter, inflation of the intermediary balloon causes the balloon to press against the inner surface of the containment device 20 to thereby secure the containment device 20 in place. Alternatively, the cannulated sleeve 210 may be coupled to the containment device 20 via deformation of an elastic element. That is, the cannulated sleeve 210 may include an inner cannulated sleeve and an outer cannulated sleeve wherein the outer cannulated sleeve is movably associated with the inner cannulated sleeve. The elastic element surrounds the inner cannulated sleeve, preferably adjacent to the distal end thereof. The inner cannulated sleeve and elastic element are inserted into the containment device 20. Thereafter the outer cannulated sleeve is moved relative to the inner cannulated sleeve so that the distal end of the outer cannulated sleeve contacts the elastic element. Continued movement of the outer cannulated sleeve causes the elastic element to deform, resulting in the elastic element increasing in diameter, which, in turn, causes the elastic element to press against the inner surface of the containment device 20. Alternatively, the outer cannulated sleeve may be coupled to an elastic compression ring so that movement of the inner cannulated sleeve with respect to the outer cannulated sleeve causes the inner cannulated sleeve to contact and subsequently compress the elastic compression ring, which in turn causes the compression ring to expand and press against the containment device 20.

Moreover, the cannulated sleeve 210 may be coupled to the containment device 20 by a heat sensitive connection. That is, the containment device 20 may be attached to or incorporate a heat sensitive element. Thereafter, as the injected bone cement hardens, the resulting increase in temperature melts the heat sensitive element enabling the containment device 20 to be decoupled from the cannulated sleeve 210.

Furthermore, the cannulated sleeve 210 may be coupled to the containment device 20 by an intermediate clamping element. That is, the cannulated sleeve 210 may include an inner cannulated sleeve and an outer cannulated sleeve wherein the outer cannulated sleeve is movably associated with the inner cannulated sleeve. The intermediate clamping element may be formed on or coupled to the inner cannulated sleeve, preferably on the outer surface of the inner cannulated sleeve adjacent to a distal end thereof. The containment device 20 is thereafter placed between the inner cannulated sleeve and the intermediate clamping element. Thereafter movement of the outer cannulated sleeve with respect to the inner cannulated sleeve causes the outer cannulated sleeve to move over the intermediate clamping element thus securing the containment device.

In addition, the cannulated sleeve 210 may be integrally formed with the containment device 20. The integrally formed cannulated sleeve and containment device may be separated by a predefined breaking region such that during the procedure the containment device 20 be separated from the cannulated sleeve 210 by rupturing the breaking region.

Preferably, as shown in FIGS. 10A and 10B, the porous containment device 20 may be designed so that it includes a connecting part 300. The connecting part 300 may be sized and configured to slidably receive a proximal end 211 of an inner cannulated sleeve 210. Once the connecting part 300 is slipped over the proximal end 211 of the inner cannulated sleeve 210, the connecting part 300 can be secured between the outer surface 212 of the inner cannulated sleeve 210 and an inner surface 331 of an outer cannulated sleeve 330. That is, the connecting part 300 of the containment device 20 may be pinched between the outer surface 212 of the inner cannulated sleeve 210 and an inner surface 331 of the outer cannulated sleeve 330. Preferably, the outer cannulated sleeve 330 can be inserted over at least a portion of both the connecting part 300 and the inner cannulated sleeve 210.

More specifically, the inner cannulated sleeve 210 preferably includes a groove 215 formed adjacent to the proximal end 211 thereof. The groove 215 being sized and configured to receive at least a portion of the connecting part 300. After at least a portion of the connecting part 300 is located within the groove 215, the outer cannulated sleeve 330 can be moved distally with respect to the inner cannulated sleeve 210 so that at least a portion of the connecting part 300, which is located within the groove 215, is sandwiched between the outer surface 212 of the inner cannulated sleeve 210 and the inner surface 331 of the outer cannulated sleeve 330. In use, the diameter of the outer cannulated sleeve 330 is preferably only a few millimeters bigger than the outer diameter of the inner cannulated sleeve 210. More preferably, the difference in diameters between the outer cannulated sleeve 330 and the inner cannulated sleeve 210 is less than the thickness of the porous containment device 20. Alternatively, the containment device 20 may be formed with a thicker proximal end so that the thicker end can be inserted into the groove 215 formed adjacent to the proximal end 211 of the inner cannulated sleeve 210. Thereafter, the outer cannulated sleeve 330 can be moved distally with respect to the inner cannulated sleeve 210 securing the thicker end in the groove 215 without pinching or deforming the containment device 20. Moreover, it is envisioned that the thicker end can be manufactured as a separate component and coupled to the containment device 20. Alternatively, the thicker end can be integrally formed via, for example, a hot stamp.

Once the porous containment device 20 has been coupled to the cannulated sleeve 210, the sleeve 210 and porous containment device 20 may be inserted into the targeted vertebral body V via a small hole formed in the targeted vertebral body V. A guide wire or similar type structure (not shown) may be initially attached to the distal end of the sleeve 210 in order to prevent uncontrolled folding of the containment device 20 during insertion into the targeted vertebral body V. The guide wire is removed once the containment device 20 is properly positioned. The position of the containment device 20 can be monitored on a radiographic imaging system such as, for example, a C-arm, an X-ray, etc. with the assistance of one or more radiolucent markers such as radiopacity rings or markers 65 previously described. The porous containment device 20 is detachable from the sleeve 210 once the containment device 20 is expanded via injection of the bone filler material 50 through the cannulated sleeve 210 so that the porous containment device 20 and the injected bone filler material 50 remains within the interior volume 2 of the targeted vertebral body V. Preferably, the sleeve 210 includes a check valve to ensure that bone filler material 50 flows only in one direction through the sleeve 210 and into (but not back out of) the porous containment device 20.

An exemplary surgical method in accordance with one aspect of the present invention includes forming a small targeted incision in the patient's skin. An extra- or trans-pedicular approach is preferably chosen. More preferably, a bipedicular approach is chosen so that two porous containment devices 20 can be simultaneously expanded within the patient's vertebral body. A guide wire or Yamshidi needle with a working cannula 100 is inserted under C-arm control. A tap may be inserted with the working cannula 100 over the guide wire, if a guide wire is used. The tap is then preferably removed and the working cannula 100 is left. The sleeve 210 and porous containment device 20 are then preferably inserted into the interior volume 2 of the targeted vertebral body V together with a guiding wire coupled to the distal end of the sleeve 210. The guiding wire is removed once the porous containment device 20 is properly positioned. Bone filler material 50 is then injected with adequate viscosity into the porous containment device 20 through the sleeve 210. The containment device 20 is expanded and a bone filler layer 51 is formed on the outside of the porous containment device 20, the bone filler layer 51 interdigitates with the surrounding bone tissue 4 via outflow of the bone filler material 50 through the containment device 20. The targeted vertebral body V is repositioned. Any residual bone filler material 50 remaining within the cannulated sleeve 210 is preferably pushed into the porous containment device 20 using, for example, a pusher. The sleeve 210 is decoupled from the porous containment device 20 and removed. All remaining instruments are removed and the incision is closed.

Alternatively, rather than simultaneously inserting the sleeve 210 and porous containment device 20 into the interior volume 2 of the targeted vertebral body V. A low viscous bone cement 50 may be initially injected into the cannulated sleeve 210. Thereafter, the containment device 20 may be inserted into the interior volume 2 of the targeted vertebral body V through the cannulated sleeve 210. Additional bone cement 50 may then be injected into the containment device 20 resulting in the expansion of the containment device 20. The exterior bone cement 50 securing the containment device 20 to the surrounding bone tissue 4.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A porous containment device for implantation in an interior volume of a targeted vertebral body, the porous containment device comprising an outer surface defining an interior cavity for receiving a bone filler material; the porous containment device further including:
   a proximal portion, a distal portion, and a central portion located between the proximal and distal portions;

wherein the porous containment device is expandable from an insertion configuration to an expanded configuration via injection of a bone filler material into the interior cavity of the porous containment device and when the device is in the expanded configuration, the proximal and distal portions are enlarged and the central portion has a smaller diameter relative to the enlarged proximal and distal portions; and wherein the porous containment device includes at least one pore configured to secrete the bone filler material into an area between the enlarged proximal and distal portions, the enlarged proximal and distal portions being sized and shaped such that the secreted bone filler material is semi-contained in said area.

2. The porous containment device of claim 1, wherein the porous containment device includes at least one air or fluid evacuation pore.

3. The porous containment device of claim 2, wherein the at least one air or fluid evacuation pore is located on the enlarged proximal or distal portions.

4. The porous containment device of claim 2, wherein the at least one air or fluid evacuation pore has a diameter of about 1-49 microns.

5. The porous containment device of claim 1, wherein the at least one pore is positioned between a midline of the narrower central portion and the walls of the enlarged distal and proximal portions and has a diameter of about 50-1000 microns.

6. The porous containment device of claim 1, wherein the at least one pore is positioned between a midline of the narrower central portion and the walls of the enlarged distal and proximal portions and includes between 1 and 20 pores.

7. The porous containment device of claim 1, wherein the narrower central portion of the porous containment device includes at least one internal constraint to constrain the expansion of the narrower central portion.

8. The porous containment device of claim 1, wherein the narrower central portion of the porous containment device includes at least one external constraint to constrain the expansion of the narrower central portion.

9. The porous containment device of claim 1, wherein the proximal portion has an outer diameter D1, the distal portion has an outer diameter D2 and the central portion has an outer diameter D3, D3 being less than D1 and D2, and wherein D3 is between approximately 5% to approximately 60% of D1 and D2.

10. The porous containment device of claim 1, wherein the porous containment device further includes at least one surface enhancing structure to improve frictional contact between the porous containment device and the surrounding bone tissue when in the expanded configuration.

11. The porous containment device of claim 10, wherein the surface enhancing structure is a plurality of knobs or ribs formed on the outer surface of the porous containment device designed to direct the secreted bone filler material.

12. The porous containment device of claim 1 further comprising a connecting part sized and configured to connect with a cannulated sleeve.

13. A cannulated sleeve detachably coupled to the porous containment device of claim 1, the cannulated sleeve comprising an inner cannulated sleeve having an outer surface, an outer cannulated sleeve having an inner surface, and having a proximal end designed to engage a portion of the porous containment device.

14. A cannulated sleeve detachably coupled to the porous containment device of claim 12, the cannulated sleeve comprising an inner cannulated sleeve having an outer surface, an outer cannulated sleeve having an inner surface, and having a proximal end designed to engage the connecting part of the porous containment device.

15. The cannulated sleeve of claim 14, wherein the connecting part of the porous containment device is sized and configured to slidably receive the proximal end of the inner cannulated sleeve such that the connecting part is secured between the outer surface of the inner cannulated sleeve and the inner surface of the outer cannulated sleeve.

16. The cannulated sleeve of claim 14, wherein the inner cannulated sleeve includes a groove formed adjacent to the proximal end, and the groove is sized and configured to receive at least a portion of the connecting part.

17. The cannulated sleeve of claim 16, wherein at least a portion of the connecting part of the porous containment device is located within the groove such that the connected part is sandwiched between the outer surface of the inner cannulated sleeve and the inner surface of the outer cannulated sleeve.

18. A porous containment device for implantation in an interior of a vertebral body, the porous containment device having a cavity for receiving a bone filler material; the porous containment device further including:

an enlarged proximal portion, an enlarged distal portion, and a narrower central portion located between the enlarged proximal and distal portions, the narrower central portion having a smaller diameter relative to the enlarged proximal and distal portions;

wherein the porous containment device is expandable from an insertion configuration to an expanded configuration via injection of a bone filler material into the cavity of the porous containment device; and wherein the narrower central portion of the porous containment device includes at least one pore for secreting the bone filler material and the enlarged proximal and distal portions do not include pores, the at least one pore being positioned between the enlarged distal and proximal portions.

19. A porous containment device for implantation in an interior of a vertebral body, the porous containment device having a cavity for receiving a bone filler material; the porous containment device further including:

enlarged proximal and distal portions including at least one fluid evacuation pore having a first diameter, and a narrower central portion located between the enlarged proximal and distal portions, the narrower central portion having a smaller diameter relative to the enlarged proximal and distal portions and having at least one bone filler material pore for secreting bone filler material, the at least one bone filler material pore having a second diameter that is greater than the first diameter;

wherein the porous containment device is expandable from an insertion configuration to an expanded configuration via injection of bone filler material into the cavity.

* * * * *